(12) United States Patent
Nakazato

(10) Patent No.: US 7,416,708 B2
(45) Date of Patent: Aug. 26, 2008

(54) METHOD OF MEASURING PROTEIN SOLUBILITY, PROCESS FOR PRODUCING CRYSTAL AND APPARATUS THEREFOR

(75) Inventor: Katsuyoshi Nakazato, Tokyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/550,062

(22) PCT Filed: Oct. 10, 2003

(86) PCT No.: PCT/JP03/13057

§ 371 (c)(1),
(2), (4) Date: Jan. 27, 2006

(87) PCT Pub. No.: WO2004/090515

PCT Pub. Date: Oct. 21, 2004

(65) Prior Publication Data

US 2006/0228805 A1    Oct. 12, 2006

(30) Foreign Application Priority Data

Apr. 1, 2003   (JP) .............................. 2003-097984

(51) Int. Cl.
*B01D 9/02* (2006.01)

(52) U.S. Cl. ..................................... 422/245.1; 117/202

(58) Field of Classification Search .................. 422/102, 422/245.1; 436/522; 117/4, 5, 206, 919, 117/925, 68, 81, 14, 15, 18, 202

See application file for complete search history.

(56) References Cited

U.S. PATENT DOCUMENTS

| 4,717,827 | A | * | 1/1988 | Harvey | ....................... 250/343 |
| 5,362,325 | A | * | 11/1994 | Shiraishi et al. | ............. 117/201 |
| 2002/0115225 | A1 | * | 8/2002 | Wagner et al. | .............. 436/518 |

* cited by examiner

*Primary Examiner*—Jill Warden
*Assistant Examiner*—Natalia Levkovich
(74) *Attorney, Agent, or Firm*—Young & Thompson

(57) ABSTRACT

Efficient measuring of protein solubility with the use of a precipitating agent as crystallization parameter; and production of a high-quality protein crystal with the use of a solubility curve obtained by the measuring. Protein crystal is disposed, and the surrounding thereof is filled with a protein solution. Not only is the concentration of precipitating agent in the protein solution increased but also the interference fringes of the protein solution around the crystal are observed, and in which of dissolution, growth and equilibrium the condition of crystal resides is judged from the interference fringes. The protein concentration of protein solution is simultaneously measured, and the solubility, of protein is determined from the observation results of interference fringes together with the measured protein concentration and precipitating agent concentration. Further, a solubility curve is prepared, and a protein crystal is produced through controlling of supersaturation condition.

8 Claims, 7 Drawing Sheets

Fig.5  Absorption spectrum of lysozyme
(light path length : 0.30 mm)

Fig. 6 Lysozyme concentration dependence of absorbance

METHOD OF MEASURING PROTEIN SOLUBILITY, PROCESS FOR PRODUCING CRYSTAL AND APPARATUS THEREFOR

TECHNICAL FIELD

To analyze stereostructure of biopolymers such as proteins and DNAs by high resolution, a first task should be to produce a single crystal of a biopolymer with a high quality. To obtain high-quality protein crystals, it is necessary to control the supersaturation state of a biopolymer solution during the process of crystal growth. For controlling the supersaturation state, information on the solubility of the biopolymer is indispensable.

The present invention relates to a technology for measuring the solubility of a biopolymer; in particular a protein and to a technology for producing protein crystals.

In the crystallization of protein, temperature, concentration of protein, concentration of a precipitating agent, pH and so on are used as crystallization parameters.

The present invention relates to a technology for measuring protein solubility using the concentration of a precipitating agent such as a salt or polyethylene glycol as a parameter and to a technology for producing protein crystals by utilizing the information on a solubility curve obtained by measuring the protein solubility.

BACKGROUND ART

The twenty first century is said to be an era of life science. In the life science, proteins have attracted much attention in the post-genome generation and it is important to clear the three-dimensional structures of the proteins with an atom resolution level in order to clarify the correlations between the structure and function of proteins.

In particular, proteins such as enzymes and receptors are main targets of medicines, so that the information on the three-dimensional structures of proteins is important for drug design in the development of medicines.

One of the most frequently used method for analyzing the three-dimensional structure of proteins is X-ray crystal structure analysis. To perform this, a high-quality single crystal must be made.

Use of a crystal of a higher quality without lattice defects enables analyses with a higher precision. At present, however, it is difficult to obtain a high-quality single crystal of a protein. This is a bottle neck in the structure analysis of proteins.

In particular, it is very important to measure the solubility of a protein, which is a basic data for producing protein crystals. In actuality, however, the measurement of solubility of proteins has scarcely been performed since much sample is necessary to do so and it takes a few weeks to a few months to obtain results.

In recent years, methods that allow measurement of solubilities using a relative small amount of sample in a short time have been developed. Such methods include, for example, an optical interference method involving use of a two-beam interferometer (cf., Non-patent documents 1 to 3), a scintillation method, and a microcolumn method.

However, these methods require proteins in an amount of 100 mg or more, even if they are a little amount, by finally getting solubility curves.

<Technology for Producing Protein Crystals>

At present, typical examples of the technology for producing protein crystals include a vapor diffusion method that involves use of the concentration of a protein and the concentration of a precipitating agent as crystallization parameters and a dialysis method that involves use of the concentration of a precipitating agent as a crystallization parameter.

(Vapor Diffusion Method)

This is a method of producing protein crystals by setting a high-concentration protein solution to which a precipitating agent is added, in the form of small droplets in a sealed vessel, filling a salt solution adjusted to a predetermined concentration, which defines the evaporation rate of water, usually, the concentration of which is approximately double the concentration of the precipitating agent in the initial protein solution, and gradually evaporating water from the droplets of the protein solution to precipitate and grow protein crystals in the droplets.

Known methods of this type include a sitting drop method and a hanging drop method. Both the methods have defects. For example, it is difficult to control the amount of water evaporated from the droplets and in addition oxidation denaturation of proteins tends to proceed due to contact of the protein solution with a layer of air.

(Dialysis Method)

This is a method using a semipermeable membrane. Specific examples thereof include a method using a button-shaped cell having small chambers (hereafter, also referred to as "microcell") and a semipermeable membrane. This is a method of producing protein crystals by charging a small amount, for example, 5 μl of a protein solution adjusted its concentration (containing a precipitating agent in advance if desired) into the small chambers of the cell, sealing the openings of the small chambers with a semipermeable membrane, and immersing the cell in a salt solution with a high concentration to gradually increase the salt concentration in the protein solution in the small chambers by utilizing the phenomenon of dialysis diffusion, thereby precipitating and growing protein crystals in the small chambers.

With the above-mentioned methods, once the apparatus is set, it is only necessary to wait until crystals are generated and grown, it is thus difficult to control the growth of the crystals positively.

Besides, the known methods for producing protein crystals include a batch method that involves preparing a protein solution with a supersaturated state from the beginning and allowing the protein solution to stand to anticipate to generate and grow crystals and a liquid-liquid diffusion method that involves mixing a protein solution and a salt solution by diffusion of solutes to produce crystals. However, it is difficult for the methods that have been ever developed to control the degree of supersaturation that is important for preparing high-quality protein crystals.

<Document Name>

Non-patent document 1: G. Sazaki, et al., J. Crystal Growth, 169(1996)355

Non-patent document 2: G. Sazaki, et al., J. Crystal Growth, 169(1999)204

Non-patent document 3: K. Ninomiya, et al., J. Crystal Growth, 222(2001)311

DISCLOSURE OF INVENTION

Figure 1:
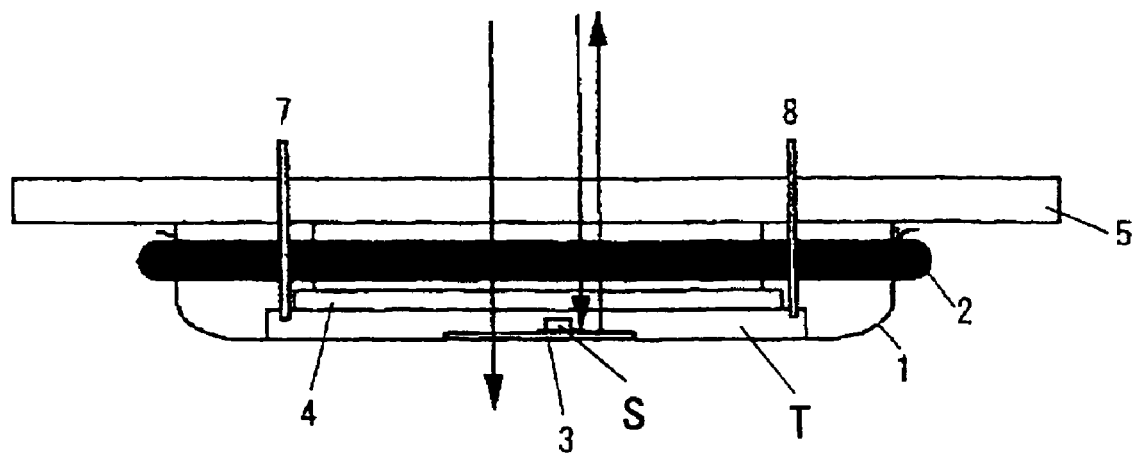
FIG. 1 is a cross-sectional view of an inner vessel (button shaped dialysis cell) portion of a dialysis cell.

The present invention has been made to solve the problems in the conventional technologies as described above, and provides a method and an apparatus of measuring a protein solubility using an extremely small amount of protein, for example, a few milligrams (mg), in a short time without the fear of protein denaturation and with accuracy.

Further, the present invention provides a method and an apparatus capable of producing high-quality protein crystals accurately and extremely efficiently by controlling growth conditions of protein crystals, in particular degree of supersaturation based on a highly reliable solubility curve prepared using the numerical values of obtained solubility.

To obtain high-quality single crystals of a protein, it is necessary to obtain information on the solubility of the protein.

Accordingly, the inventor of the present invention have first made extensive studies on a method and an apparatus of measuring the solubility of a protein crystal by using precipitating agents as parameter, such as salts and polyethylene glycol (PEG) that are used most frequently in crystallizing proteins. As a result, the following invention has been completed.

(1) A method of measuring a solubility of a protein with respect to a concentration of the precipitating agent, comprising observing interference fringes formed around a protein crystal using a two-beam interferometer while increasing or decreasing the concentration of the precipitating agent in the protein solution filled around the protein crystal, wherein the concentration of the protein solution filled around the protein crystal is measured and the interference fringes are observed.

(2) The method of measuring a solubility of a protein with respect to a concentration of the precipitating agent according to above item (1), wherein the method comprises: providing a quartz thin plate having a light reflecting thin film on a portion of the front side surface or back side surface thereof; mounting the protein crystal on a portion of the quartz thin plate where the light reflecting thin film is provided; observing the interference fringes formed around the protein crystal; and measuring the concentration of the protein in the protein solution through a portion of the quartz thin plate where light reflecting thin film is not provided, whereby performing measurement of the concentration of the protein solution filled around the protein crystal and observation of the interference fringes.

(3) The method according to above item (1) or (2), wherein the concentration of the precipitating agent in the protein solution filled around the protein crystal is increased or decreased by adjusting the concentration of a contained precipitating agent solution separated from the protein solution via a dialysis membrane.

(4) The method according to any one of above items (1) to (3), wherein the solubility of the protein is determined from the concentration of the protein solution and the concentration of the precipitating agent when the interference fringes formed around the protein crystal observed using the two-beam interferometer are constituted by straight lines that do not curve in the vicinity of the protein crystal.

(5) The method according to any one of above items (1) to (4), wherein the concentration of the protein in the protein solution is measured by a spectrophotometer.

(6) A method of preparing a solubility curve of a protein with respect to a concentration of a precipitating agent, comprising: changing stepwise a concentration of a protein in a protein solution filled around a protein crystal; and obtaining a plurality of solubilities by repeating the measurement of the solubility of a protein described in any one of above items (1) to (5).

(7) The method according to above item (6), wherein the solubility curve is prepared by continuously performing the stepwise change of the concentration of the protein solution filled around the protein crystal.

(8) The method according to any one of above items (1) to (7), wherein the two-beam interferometer is a Michelson type two-beam interferometer.

(9) An apparatus of measuring a solubility of a protein with respect to a concentration of the precipitating agent, comprising: a dialysis cell having a container for containing a protein crystal and a protein solution filled around the protein crystal, and providing with a dialysis membrane; means for measuring a concentration of the protein solution; a two-beam interferometer for observing interference fringes around the protein crystal; means for increasing or decreasing a concentration of the precipitating agent in the protein solution filled around the protein crystal in the dialysis cell; and means for measuring the concentration of the precipitating agent in the protein solution filled around the protein crystal in the dialysis cell.

(10) The apparatus according to above item (9), wherein the dialysis cell comprises: a quartz thin plate for mounting the protein crystal, having a light reflecting thin film on a portion of the front side surface or back side surface thereof; an inner vessel containing the quartz thin plate therein, provided with a surface portion covered with a dialysis membrane and filled with the protein solution therein; and an outer vessel filled with the protein precipitating agent solution outside the dialysis membrane.

(11) The apparatus according to above item (9) or (10), wherein the means for measuring the concentration of the protein solution is a spectrophotometer.

(12) The apparatus according to above item (11), wherein the spectrophotometer measures an intensity of transmitted light that transmits a portion of the quartz thin plate in the dialysis cell where light reflecting thin film is not provided.

(13) The apparatus according to any one of above items (9) to (12), further comprising means for sending the precipitating agent solution to the outer vessel of the dialysis cell while continuously increasing or decreasing the concentration of the precipitating agent.

(14) The apparatus according to any one of above items (9) to (13), further comprising means for introducing the protein solution having a desired concentration or a diluent solution into the inner vessel of the dialysis cell without disassembling the dialysis cell.

(15) The apparatus according to any one of above items (9) to (14), further comprising means for photographing the interference fringes by the two-beam interferometer, such as a CCD camera.

(16) The apparatus according to any one of above items (9) to (15), wherein the two-beam interferometer is a Michelson type two-beam interferometer.

(17) A dialysis cell for an apparatus measuring a solubility of a protein, comprising: a quartz thin plate for mounting the protein crystal, having a light reflecting thin film on a portion of the front side surface or back side surface thereof; an inner vessel for containing the quartz thin plate, provided with a surface portion covered with a dialysis membrane and filled with the protein solution therein; and an outer vessel filled with the precipitating agent solution outside the dialysis membrane.

(18) A method of producing a protein crystal by utilizing a solubility curve prepared by the method according to above item (6) or (7) while controlling a degree of supersaturation of a protein solution around a growing protein crystal.

(19) An apparatus of producing a protein crystal, comprising: a dialysis cell having a container for containing a protein crystal and a protein solution filled around the protein crystal, and provided with a dialysis membrane; means for controlling a concentration of the protein in the protein solution around the protein crystal; means for measuring a concentration of the protein solution around the protein crystal; a two-beam interferometer for observing interference fringes around the protein crystal; means for controlling a concentration of the precipitating agent in the protein solution around the protein crystal; and means for measuring the concentration of the precipitating agent in the dialysis cell.

(20) The apparatus according to above item (19), wherein the dialysis cell comprises: a quartz thin plate for mounting the protein crystal, and provided a light reflecting thin film on a portion of the front side surface or back side surface thereof; an inner vessel for containing the quartz thin plate therein, provided with a surface portion covered with a dialysis membrane and filled with the protein solution therein; and an outer vessel filled with the precipitating agent solution outside the dialysis membrane.

(21) The apparatus according to above item (19) or (20), wherein the means for measuring the concentration of the protein solution is a spectrophotometer.

(22) The apparatus according to above item (21), wherein the spectrophotometer measures an intensity of transmitted light that transmits a portion of the quartz thin plate in the dialysis cell where light reflecting thin film is not provided.

(23) The apparatus according to any one of above items (19) to (22), further comprising means for sending the precipitating agent solution having a desired concentration to the outer vessel of the dialysis cell.

(24) The apparatus according to any one of above items (19) to (23), further comprising means for introducing the protein solution having a desired concentration into the inner vessel of the dialysis cell without disassembling the dialysis cell.

(25) The apparatus according to any one of above items (19) to (24), further comprising means for photographing the interference fringes by the two-beam interferometer, such as a CCD camera.

(26) The apparatus according to any one of above items (19) to (25), wherein the two-beam interferometer is a Michelson type two-beam interferometer.

(27) A dialysis cell for an apparatus for producing a protein crystal, comprising: a quartz thin plate for mounting the protein crystal, provided a light reflecting thin film on a portion of the front side surface or back side surface thereof; an inner vessel for containing the quartz thin plate therein, provided with a surface portion covered with a dialysis membrane and filled with the protein solution therein; and an outer vessel filled with the precipitating agent solution outside the dialysis membrane.

BEST MODE FOR CARRYING OUT THE INVENTION

Hereinafter, the present invention is explained successively with reference to the attached drawings.

Figure 7:
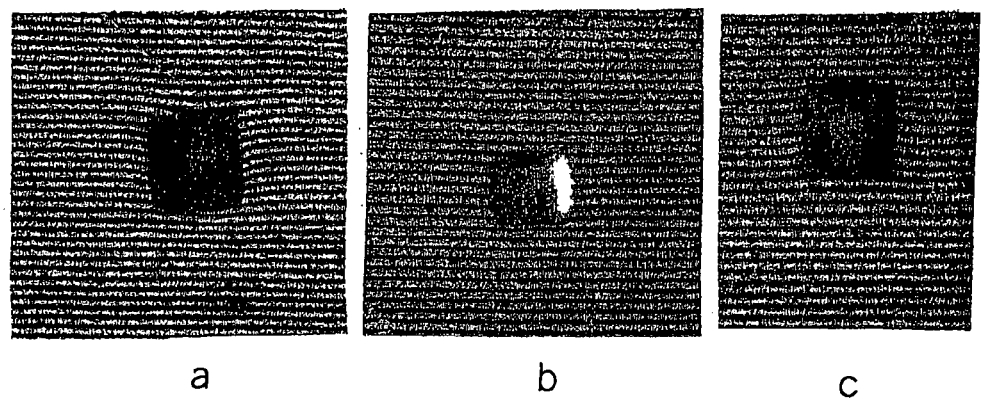
FIG. 7 is a diagram showing interference fringes in accordance with a growing state of a crystal, and "a" indicates the pattern of the interference fringes when the crystal is growing, "b" indicates the pattern of the interference fringes when the crystal is in an equilibrium state, and "c" indicates the pattern of the interference fringes when the crystal is being dissolved.

The present invention employed an optical interferometry using a two-beam interferometer utilizing light such as laser beam and first the principle thereof is outlined (cf. FIG. 7).

In a state where a protein crystal is growing in a protein solution at a certain value of crystallization parameter, as the crystal incorporates the protein of a solute from the solution around the crystal, the protein concentration in the solution immediately around the crystal is lower than that in the solution outer from the solution immediately around the crystal.

In this state, when one of beams split by a splitter is applied to the vicinity of the crystal and the other beam is reflected from a mirror, the interference fringes made from both beams are seen to be curved since the optical refractive index decreases around crystal to make the optical path shorter (cf. FIG. 7a).

When the crystal and the solution are in equilibrium state, the interference fringes are seen like straight parallel lines since the concentration of protein in the solution immediately around the crystal and that of the solution outer from the solution immediately around the crystal are the same (cf. FIG. 7b).

When the crystal is in a dissolving state, the protein concentration immediately around the crystal increases, so that the interference fringes are seen to be curved in the direction opposite to that in the case where crystal is growing (FIG. 7c).

Application of light to the vicinity of the crystal and observation of interference fringes of transmitted light reveal the protein concentration distribution immediately around the crystal, with the result that whether the crystal is growing or is being dissolved or in an equilibrium state can be judged.

Therefore, the solubility of the protein crystal with respect to the concentration of the precipitating agent can be obtained by determinating the concentration of the precipitating agent and that of the protein when they are in an equilibrium state.

The interference fringes can be observed with naked eye. Further, efficient observation of the interference fringes can be performed by using continuous automatic photography, in particular by use of auto-recording means using a CCD camera or the like.

The principle of the optical interferometry using a two-beam interferometer is also described in detail in the above-mentioned Non-patent documents 1 to 3.

Now, the measurement of the solubility of a protein in the present invention is described.

A thin plate of quartz or quartz glass (hereafter, also referred to as "quartz" simply) is provided and a thin film for reflecting light is formed on a protein of the front side surface or back side surface of the quartz thin plate, preferably on a half of one side of the quartz thin plate.

The thin film for reflecting light may be made of any material that reflects light reliably. Preferably, the thin film can be made by deposition of gold.

The portion provided the thin film for reflecting light is a place where the crystal is mounted and light for measuring interference fringes is reflected.

The portion without the thin film for reflecting light on the quarts thin plate is a portion where the light for measuring concentration of a protein passes through; the protein concentration is measured by absorption analysis of transmitted light using a spectrophotometer.

Then, the crystal of a protein to be measured is mounted on the portion of the quartz thin plate where the thin film for reflecting light is provided together with a small amount of a crystallization mother liquor, and the resultant is placed in an inner vessel.

The opening of the inner vessel is covered with a dialysis membrane. To fix the dialysis membrane to the inner vessel, an elastic O-ring is preferably used.

The pore size of the dialysis membrane can be appropriately selected depending on the molecular weight and shape of the protein.

The protein solution is flowed into the dialysis cell through a pipe on the upper part of the dialysis cell to fill the protein solution having predetermined concentration in the inner vessel in the dialysis cell.

Figure 2:
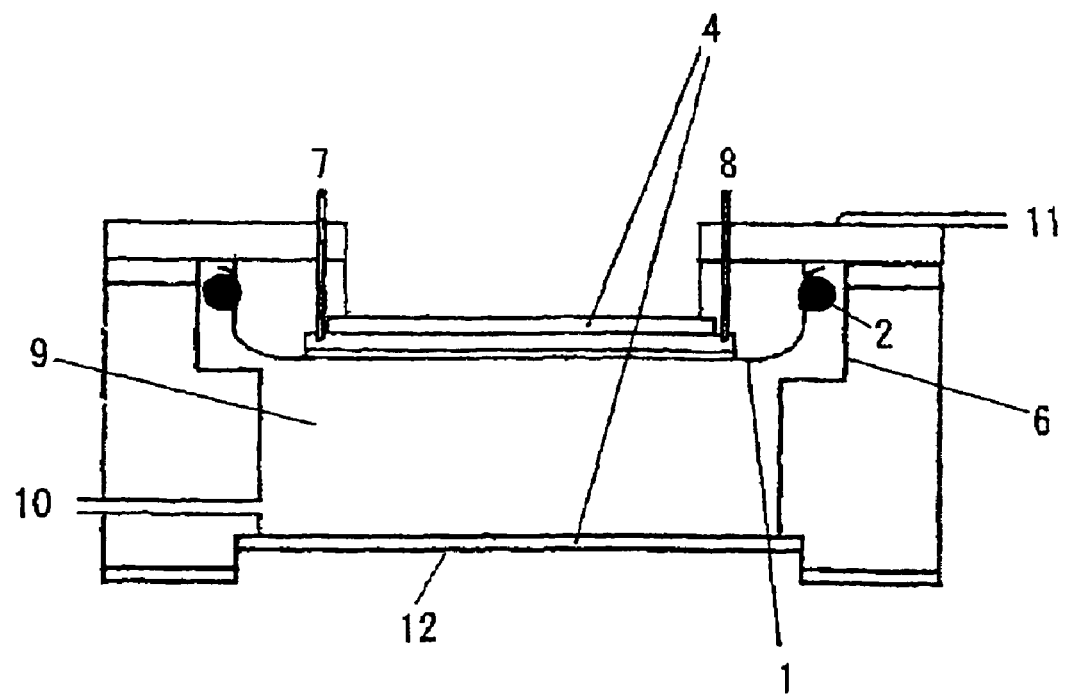
FIG. 2 is a cross-sectional view of the dialysis cell.
Figure 3:
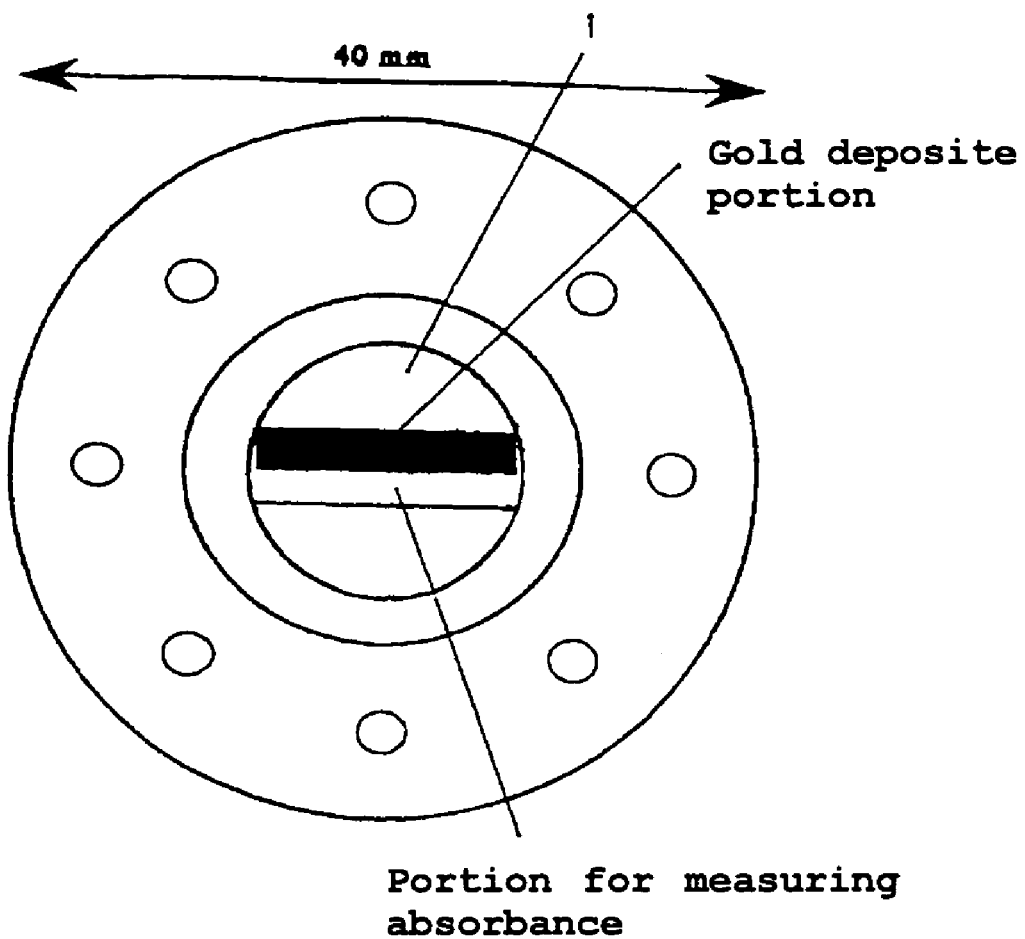
FIG. 3 is a top view of the dialysis cell.

Specific examples of the dialysis cell are shown in FIG. 1 to 3 when measuring the solubility of a protein.

FIG. 1 shows an inner vessel that contains the protein crystal and protein solution in a dialysis cell, illustrating the state that the protein crystal (S) to be measured is contained together with the protein solution (T).

In FIG. 1, 1 denotes a dialysis membrane, 2 denotes an elastic O-ring for fixing the dialysis membrane to a dialysis cell, and 3 denotes a quartz thin-plate having provided on a portion of the surface thereof a gold deposition layer (Au) that is a layer of a thin film for reflecting light (also referred as a light reflecting layer). 4 denotes a quartz glass thin plate arranged via a spacer, 5 denotes a flange section, 7 and 8 denote an inflow pipe and an outflow pipe for the protein solution as means for flowing the protein solution having desired concentrations into the inner vessel of the dialysis cell without disassembling the dialysis cell.

In the vicinity of the protein crystal, the arrow mark that is reversed at the portion of the light reflecting layer indicates a light path of a laser beam for measuring the distribution of concentration of the protein solution around the crystal as interference fringes. The arrow mark that passes through the portion of the quarts thin plate where light reflecting layer is not provided indicates a light path of beam from another light source for measuring the concentration of the protein in the protein solution.

FIGS. 2 and 3 are a side cross-sectional view (FIG. 2) and a top view (FIG. 3) of the dialysis cell which is a combination of an inner vessel that contains the protein crystal and the protein solution shown in FIG. 1 and an outer vessel that contains an external dialysate comprising a solution of a precipitating agent.

Figure 6:
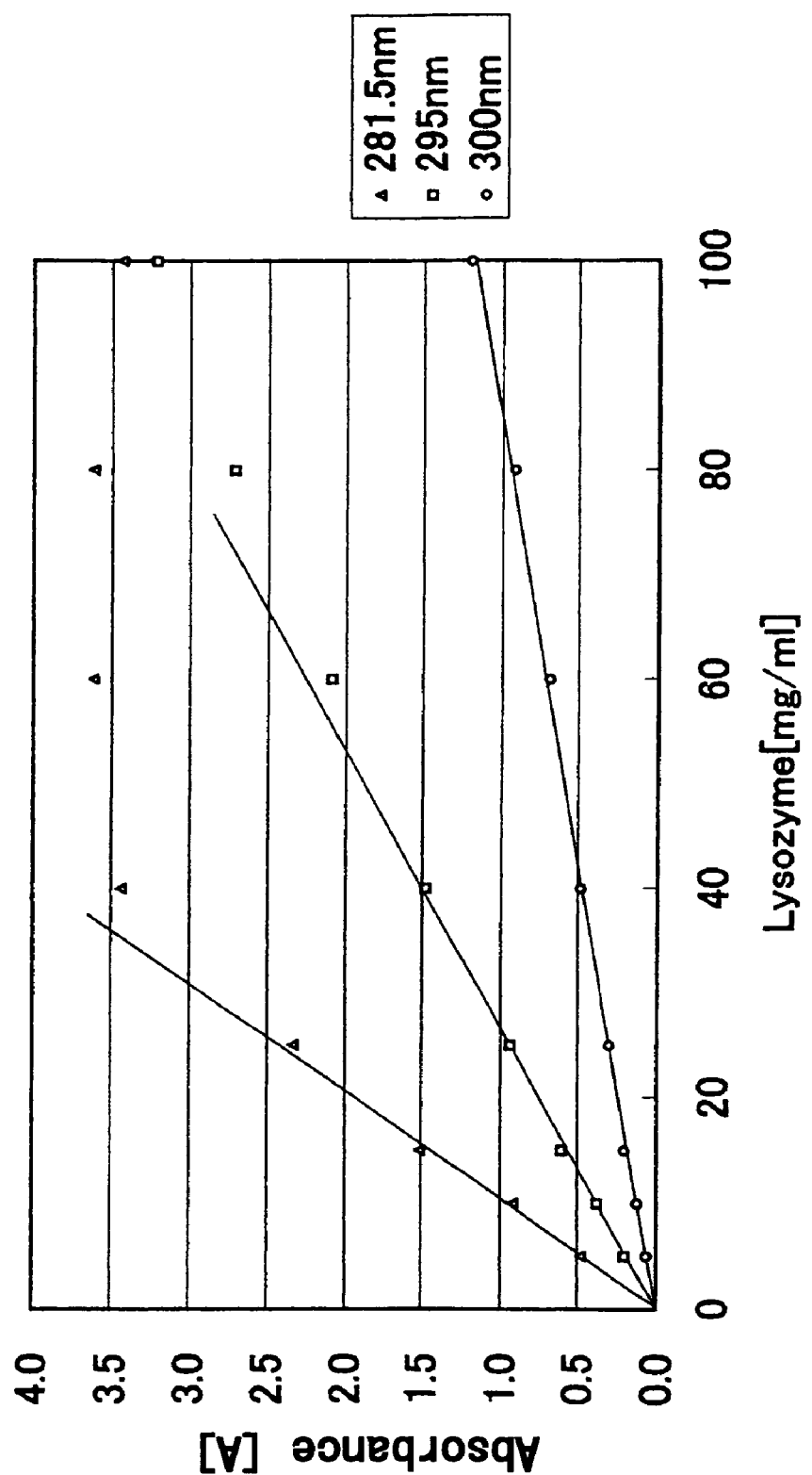
FIG. 6 shows lysozyme concentration dependence of absorbance.

In FIGS. 2 and 3, 6 denotes a dialysis cell fixing plate, 9 denotes a dialysis outer liquid chamber of the outer vessel, which is provided with means for stirring the dialysis outer liquid, such as a magnetic stirrer. 10 denotes an inflow pipe for the dialysis outer liquid, and 11 denotes an outflow pipe for the dialysis outer liquid. 12 denotes a window glass for spectroscopy that forms the bottom of the dialysis outer liquid chamber.

Figure 4:
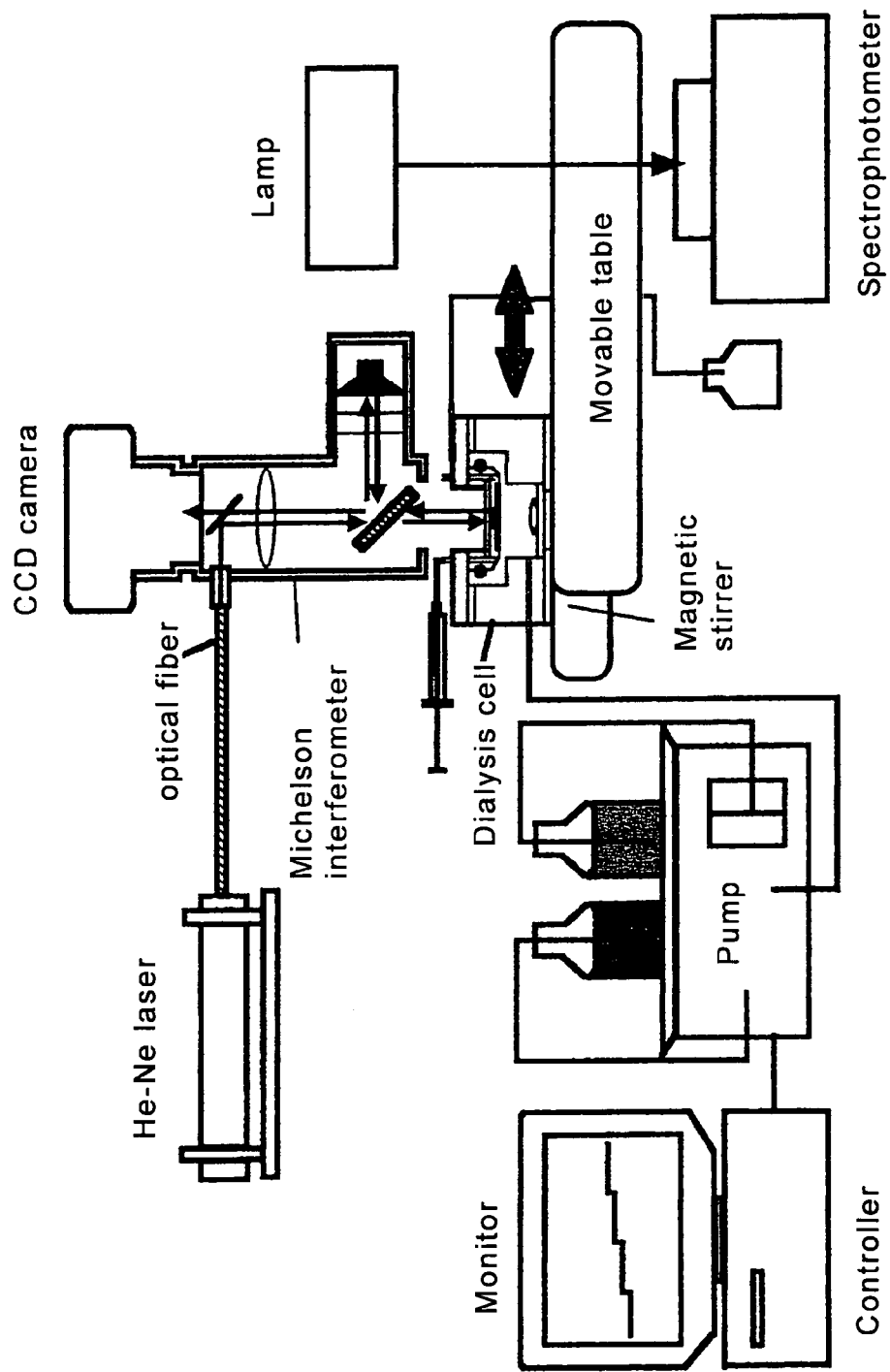
FIG. 4 is a schematic diagram showing a state for measuring interference fringes by a two-beam interferometer.

A solubility measuring apparatus as shown in FIG. 4 is assembled by using the dialysis cell thus assembled to measure the solubility of the protein.

FIG. 4 is a schematic diagram showing an apparatus for observing the protein concentration distribution in the protein solution around the protein crystal mounted in the dialysis cell using a Michelson type two-beam interferometer and photographing the observed interference fringes with a CCD camera.

The laser beam from a light source (not shown) is split into two by a beam splitter. One beam is sent to the dialysis cell and the other beam is sent to a reflecting mirror.

The reflected light from the dialysis cell and the reflected light from the reflecting mirror are combined and then sent to the CCD camera to photograph the state of the interference fringes.

<Measurement of Solubility of Protein>

Measurement of solubility is performed preferably in a state such as in a thermostatic chamber or in a thermostatic bath where specified constant temperature conditions are maintained.

The protein crystal is arranged in the inner vessel of the dialysis cell, and a protein solution whose concentration is supposed to be a little bit lower or a little bit higher than the solubility of the protein crystal is filled around the crystal.

A solution of a precipitating agent is introduced into the dialysis outer liquid chamber of the dialysis cell by using means for sending the solution of a precipitating agent to the outer vessel of the dialysis cell while increasing or decreasing the concentration of the precipitating agent continuously or stepwise thereby to increase the concentration of the precipitating agent in the inner vessel of the dialysis cell by diffusion of the precipitating agent through the dialysis membrane or decrease the concentration of the precipitating agent in the inner vessel of the dialysis cell by diffusion of the precipitating agent through the dialysis membrane. As a result, the protein crystal placed in the inner vessel is transitioned from a dissolving state to a growing state via an equilibrium state, or from a growing state to a dissolving state via an equilibrium state.

In the transition step of the state of the crystal state, the shapes of the interference fringes around the crystal is observed using the means for measuring interference fringes including the Michelson type two-beam interferometer, to judge whether the crystal is in a growing state, in a dissolving state, or in an equilibrium state in the specific concentration of the protein and in the specific concentration of the precipitating agent.

The precipitating agent which is used as a parameter is not particularly limited and salts such as sodium chloride, ammonium sulfate, phosphate and polyethylene glycol (PEG) can preferably be used.

In the present invention, since the two-beam interferometer of the Michelson type preferably is used for measurement of the interference fringes, the light sent to the dialysis cell enters a sample solution and reflects on the thin film for reflecting so that the light can pass along a distance twice as compared to that in the case where the light passes simply through the sample solution.

Therefore, in the present invention, the measurement accuracy of the concentration distribution, that is, measurement accuracy of interference fringes is improved.

<Means for Measuring Concentration of Protein>

The concentration of the protein around the, crystal is measured for the intensity of transmitted light that transmits the protein solution in the portion of the quartz thin plate where light reflecting layer is not provided using a spectrophotometer. The concentration of the protein is measured at a wavelength of usually 280 nm. In measurement of the solubility of the protein, it is often difficult to measure at this wavelength even in a short optical path length because of high concentration of protein.

Figure 5:
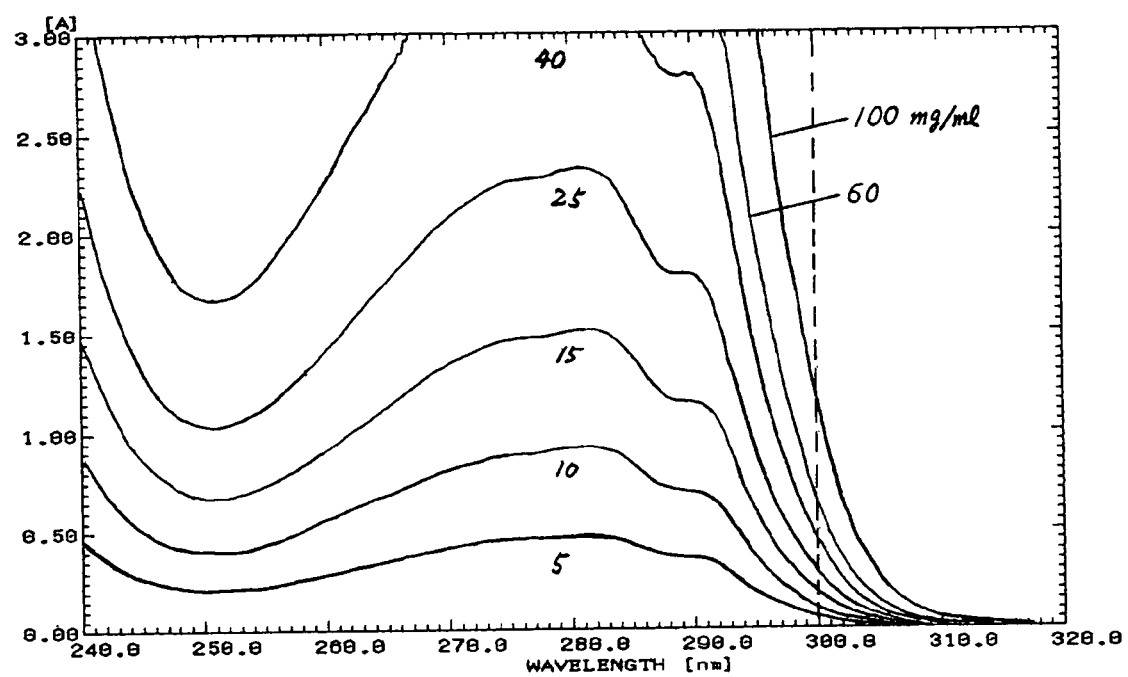
FIG. 5 shows absorption spectrum of lysozyme.

For example, as shown in FIG. 5, measurement at 280 nm is difficult if the concentration of lysozyme is above 20 mg/ml even in an optical path length of 0.30 mm.

Therefore, the inventor of the present invention performed measurements of the concentration of lysozyme and confirmed that when an optical path length of 0.30 mm and light at wavelengths of 295 nm and 300 nm are used, for example, linearity can be obtained in the measurements of the concentration up to 100 mg/ml as shown in FIG. 6.

<Means for Measuring Concentration of a Precipitating Agent in Dialysis Outer Liquid>

In the present invention, the precipitating agent must be diffused through the dialysis membrane until the concentration of the precipitating agent in the inner vessel of the dialysis cell and the concentration of the precipitating agent in the dialysis outer liquid in the outer vessel of the dialysis cell are in an equilibrium state.

To achieve this, it is effective to increase the area of the dialysis membrane in the inner vessel and decrease the amount of the protein solution to be contained therein. In addition, it is preferable to stir the dialysis outer liquid.

An equilibrium state can be established in a shorter time by stirring the protein solution in the inner vessel of the dialysis cell using, for example, a small stirring bar.

For example, in the case of the dialysis cell of the present invention, a stainless steel bar having diameter of 0.3 mm or less and length of about 5 mm can be rotated between the quartz glass thin plates 3 and 4 using a stirrer.

The stirring of the protein solution is stopped when observing the interference fringes.

It is unnecessary to directly measure the concentration of the precipitating agent in the inner vessel of the dialysis cell; it is only necessary to measure the concentration of the precipitating agent in the dialysis outer liquid that is in an equilibrium state to the solution in the inner vessel of the dialysis cell.

That is, it is only necessary to provide means for measuring the concentration of the precipitating agent in the dialysis outer liquid in the equilibrium state discharged from the outer vessel.

The means for measuring the concentration of the precipitating agent is as follows. For example, when a salt solution is used as the precipitating agent and the solutions outside and inside of the dialysis membrane are in an equilibrium state with respect to the salt solution of the precipitating agent, the concentration of the precipitating agent can be determined by measuring the electroconductivity of the dialysis outer liquid that is discharged from the outer vessel.

When the precipitating agent is not the salt solution, but PEG or the like, the concentration of PEG can be determined by mixing a high-concentration PEG solution (a known concentration) and a buffer solution in an appropriate ratio using a pump.

In this manner, the solubility of a protein can be measured accurately using a small amount of a sample in a short time from results of measurement of interference fringes that show the dissolving state of the protein crystal, a measured value of the concentration of protein around the protein crystal, and the concentration of the precipitating agent.

<Multiple Measurements of Solubility>

After measurement of solubility for a first time is completed, a protein solution having a concentration different from that of the protein solution used in the first time is filled in the inner vessel of the dialysis cell through an inflow pipe, and the measurement is performed in the same manner as described above. The solubility of the protein at the portion where the protein concentration is different can be thus measured utilizing the concentration of the precipitating agent as a parameter.

Subsequently, measurement of the solubility is repeated for a desired number of times, thereby enabling measurements of a desired number of values of solubility.

If the solubilities can be measured at plural portions, a solubility curve can be easily prepared by simply plotting the solubility values.

To perform the measurement with decreasing the amount of the protein to be used as much as possible, a first measurement is performed using a high-concentration protein solution, and then a second measurement is performed after a small amount of a diluent is introduced in the inner vessel of the dialysis bell to decrease the concentration of the protein solution. After the second measurement the concentration of the protein solutions is stepwise decreased one after another, and the measurements are performed in this manner. In this case, the used materials are only the protein crystal set in the dialysis cell at first and about 100 µl of the protein solution.

Operation of a selector valve can be coupled with an apparatus for reading interference fringes through a control system to make it possible to perform the change of the protein solutions and the diluent. It is also possible to automatically perform switching of the concentration of the protein and switching of the concentration of the precipitating agent in response to the obtained data in observation of the interference fringes. In this manner, a solubility curve of the protein can be prepared fully automatically.

<Production of Protein Crystals>

In the crystallization of a protein, the degree of supersaturation of the protein in the protein solution in the system for producing crystals directly corresponds to the degree of driving force for crystallization.

When the crystal grows in a state of a low degree of supersaturation, spiral growth of the protein crystal occurs, so that a high-quality crystal without any defect in the crystal lattice grows. With an increasing degree of supersaturation, two-dimensional nuclear growth and adhesion growth occur to cause a disturbance in the crystal lattice, so that high-quality crystals can not be obtained.

Therefore, to produce high-quality protein crystals, it is necessary to maintain the state where the degree of supersaturation is low. For this purpose, highly reliable information on solubility and accurate information on solubility curves are required.

In the present invention, protein crystals are produced using an apparatus having a structure similar to that of the apparatus used in measuring the solubility of the protein.

That is, a seed crystal of a desired protein to be crystallized is mounted on the light reflecting layer on the quartz thin plate and a state where the seed crystal does neither grow nor be dissolved, that is, an equilibrium state is detected and in this state the solubility of the protein with respect to the concentration of the precipitating agent is obtained.

Then, to cause the seed crystal to occur spiral growth to produce a high-quality protein single crystal, the concentration of the protein around the crystal is controlled to a desired supersaturation state in light of the solubility under the conditions as described above.

The desired supersaturation state can be maintained by a little bit increasing the concentration of the precipitating agent in the dialysis outer liquid in an equilibrium state and maintain the concentration as it is at the constant level while maintaining the concentration of the protein in the protein solution in the dialysis cell in an equilibrium state as it is.

Alternatively, the desired supersaturation condition can be maintained by maintaining the concentration of the precipitating agent at an equilibrium state in the dialysis outer liquid as it is while a little bit increasing the concentration of the protein in the protein solution in the dialysis cell and maintaining the concentration as it is at the constant level.

Although control becomes complex to some extent, both the concentration of the protein and the concentration of the precipitating agent may be shifted upwards or downwards along a solubility curve according to the solubility curve of the protein prepared in the present invention.

Measurement of the concentration of the protein solution around the crystal can be performed by using the portion of the quartz thin plate where light reflecting layer is not provided in the dialysis cell.

It is difficult to directly perform measurement of the concentration of the precipitating agent. However, the concentration of the precipitating agent in the liquid discharged from the outer vessel of the dialysis cell can be deemed to be the same as that of the precipitating agent in the protein solution in the inner vessel of the dialysis cell, so that the concentration in the discharged liquid can be measured instead.

EXAMPLE

Hereinafter, the present invention is explained in detail byway of examples. However, the present invention is not limited by the examples.

Example 1

Measurement of Solubility of Lysozyme Crystal

A button-shaped dialysis cell (inner vessel) of 20 mm in diameter and 0.5 mm in depth as shown in FIG. 1 was made using a quartz thin plate, an acrylic resin plate, a dialysis membrane and the like.

As dialysis membrane 1, Spectra/Por (registered trademark) Membrane MWCO: 2,000 manufactured by Spectrum Laboratories, Inc was used.

A quartz thin plate 3 (8×17 mm) of 0.2 mm in thickness deposited gold (Au) on a portion (about half along the longer side) of the surface thereof was provided and a single crystal S (about 0.2 mm cubic) of chicken egg white which is a measurement object, was mounted on the portion of the quartz thin plate where gold was deposited. The crystal of chicken egg white lysozyme was prepared by a vapor diffusion method (hanging drop method) The quartz thin plate was laminated on a quartz glass plate 4 of 1 mm in thickness via a spacer made of quartz glass of 0.31 mm in height (not shown) and the resultant was set in an inner vessel. This was assembled with an outer vessel having a reservoir chamber for a dialysis outer liquid as shown in FIGS. 2 and 3 to form a dialysis cell.

A sealing part (not shown) such as silicone rubber was arranged between the inner vessel and the outer vessel to prevent leakage of the dialysis outer liquid.

The dialysis cell was incorporated in a solubility measuring apparatus as shown in FIG. 4 (a schematic diagram of a portion that is used to measure interference fringes by a two-beam interferometer).

A solution with pH of 4.5 consisting of 100 mg/ml lysozyme, 0.1 M NaCl, and 0.05 M sodium acetate was poured into the inner vessel of the dialysis cell through a liquid inflow pipe 7.

On the other hand, a pH 4.5 buffer solution containing 0.1 M NaCl was filled in the dialysis outer liquid chamber (inner volume 3.6 ml) in advance and a precipitating agent solution was introduced into the dialysis outer liquid chamber at a flow rate of 2.0 ml/min through the dialysis outer liquid inflow pipe 10 while gradually increasing the concentration of sodium chloride from 0.1 N at the start using a two solution mixing system with two liquid transfer pumps as means for increasing the concentration of the precipitating agent in the vessel.

Mixing of the two solutions was performed using 1 M NaCl solution and a solution containing no NaCl.

Those solutions were both comprised of pH 4.5 sodium acetate buffer solutions. The dialysis outer liquid was stirred with a stirrer. The concentration of sodium chloride in the solution discharged from the dialysis outer liquid outflow pipe 11 was measured using a conductance monitor.

The crystal was changed from the dissolving state to the growing state via the equilibrium state by gradually increasing the concentration of the precipitating agent in the dialysis outer liquid. Whether the crystal is in a dissolving state, in an equilibrium state, or in a growing state was determined by observing the shape of the interference fringes around the crystal on the quartz thin plate having gold deposited thereon using a Michelson type two-beam interferometer (Nikon 2.5× 0.075 TI).

He—Ne laser was used as an optical source for the two-beam interferometer.

The change of state of the crystal was photographed using a CCD camera and results are shown in FIG. 7.

FIG. 7a shows the shape of the interference fringes when the crystal is in a growing state. FIG. 7c shows the shape of the interference fringes when the crystal is in a dissolving state. FIG. 7b shows the shape of the interference fringes when the crystal is in an equilibrium state. When the crystal is in an equilibrium state, the interference fringes of parallel lines that did not curve in the vicinity of the crystal were observed.

The concentration of the lysozyme solution around the lysozyme crystal was measured by a spectrophotometer at a wavelength of 300 nm using the portion of the quartz thin plate provided with no gold deposition as optical path.

The optical absorption of the dialysis membrane used is 0.35 or less at 300 nm and gave no disturbance in the measurement.

After completion of the first measurement, the concentration of the protein solution in the inner vessel was decreased to 80 mg/ml, and a second measurement was performed in the same manner as that in the first measurement.

The concentration of the precipitating agent was made slightly higher than that of the first time. In this manner, the measurement was performed eight times.

The concentration of the protein solution in the inner vessel was finally decreased from 100 mg/ml to 5 mg/ml. The concentration of NaCl in the precipitating agent was increased from 0.1 M to 0.7M. It is preferable that the concentration of NaCl be increased stepwise by 20 to 30 mM.

Figure 8:
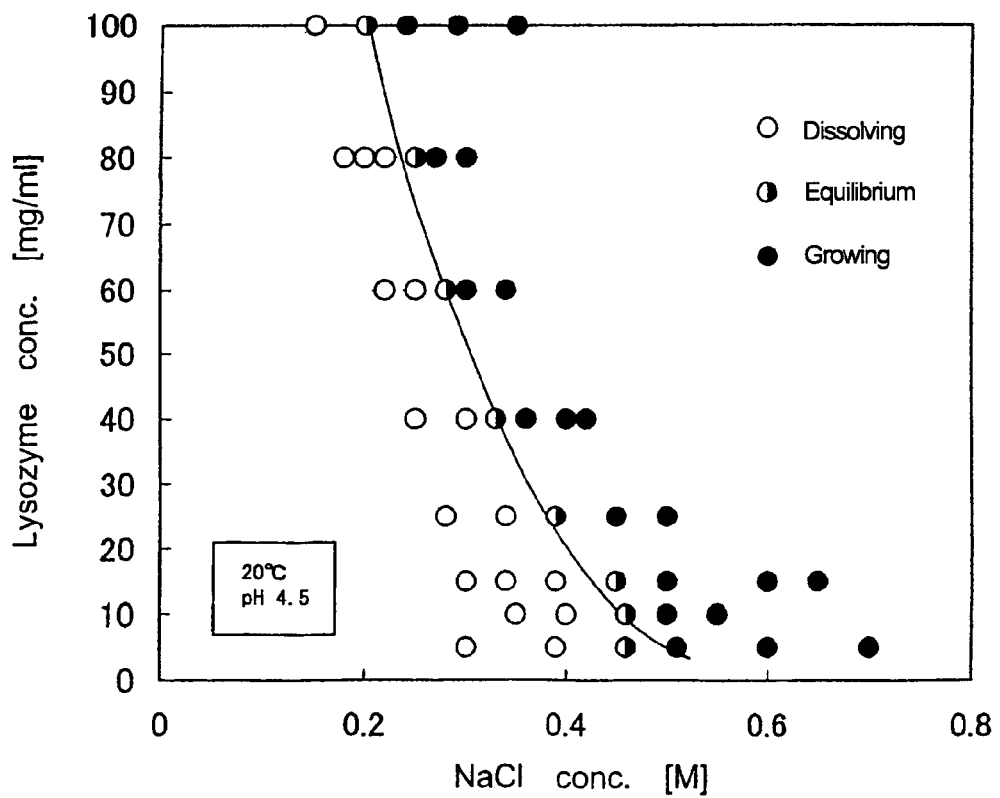
FIG. 8 is a graph showing results of observation of the interference fringes.

Results of observation of the shape of the interference fringes at a plurality of lysozyme concentrations are shown in FIG. 8.

White circles indicate a dissolving state. Semicircles indicate an equilibrium state. Black circles indicate a growing state.

A solubility curve for lysozyme using the concentration of sodium chloride as a parameter was prepared by plotting the points of semicircles that mean an equilibrium state in FIG. 8.

Comparison of the obtained solubility curve with the conventional lysozyme solubility curves revealed that they are substantially identical, confirming that the system of the present invention is valid and proper.

Example 2

Production of Lysozyme Crystals

In the inner vessel of a dialysis cell, 70 μl of a chicken egg white lysozyme solution containing 50 mg/ml chicken egg white lysozyme, 0.3 M NaCl, and 0.05 M sodium acetate and having a pH of 4.5 was set. A pH 4.5 buffer solution containing 0.3. M NaCl and 0.05 M sodium acetate was filled in the dialysis outer liquid chamber in advance. The concentration of NaCl in the inner vessel was gradually increased from 0.30 M to 0.40 M over 48 hours while changing the mixing ratio of a precipitating agent solution (1.0 M NaCl, 0.05 M sodium acetate, pH 4.5) and the buffer solution (0.5 M sodium acetate, pH 4.5) by using the mixing function of a liquid chromatography apparatus at a flow rate of 0.1 ml/min of a precipitating agent solution and the buffer solution. This process corresponds to a gradual increase in the degree of supersaturation starting from one point on the solubility curve (50 mg/ml egg white lysozyme, 0.3 M NaCl, degree of supersaturation of lysozyme being 1.0) to a supersaturation degree of lysozyme solution of 2.5 based on the results of the solubility curve obtained in Example 1 (cf. FIG. 8). Note that the degree of supersaturation is a value of $C/C_0$, wherein C is the concentration of the protein in the dialysis cell, and $C_0$ is the concentration of the protein on the solubility curve at the concentration of the precipitating agent (concentration of NaCl).

Figure 9:
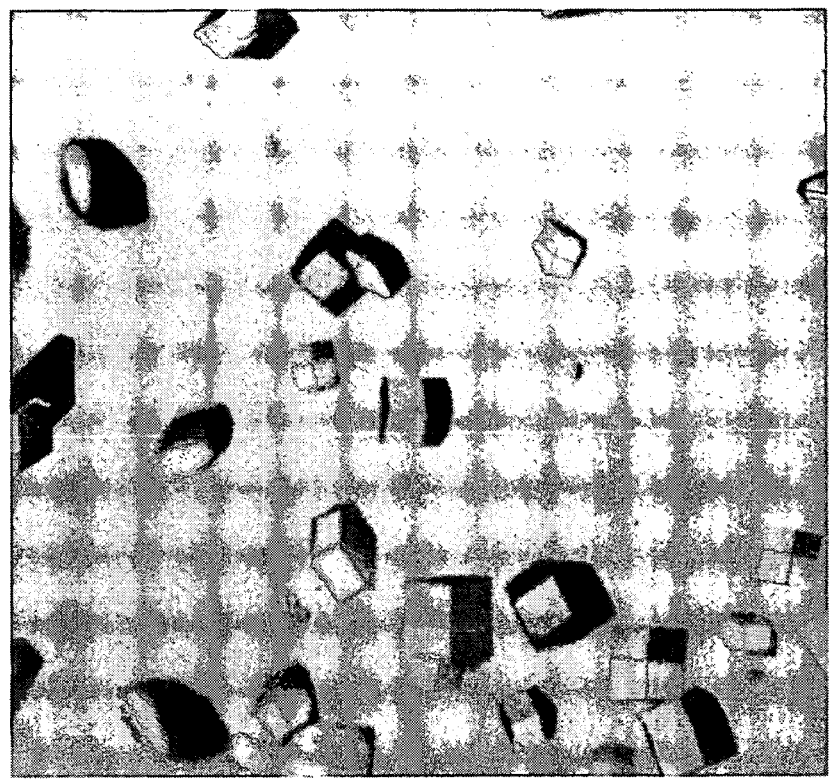
FIG. 9 is an optical micrograph of a lysozyme crystal produced in Example 2.

As a result, many high-quality lysozyme crystals of 0.05 mm cubic to 0.1 mm cubic were obtained. The obtained lysozyme crystals had a size that is fully suited for X-ray crystal analysis Optical micrograph of the obtained crystals is shown in FIG. 9.

Example 3

Production of Lysozyme Crystal

Figure 10:
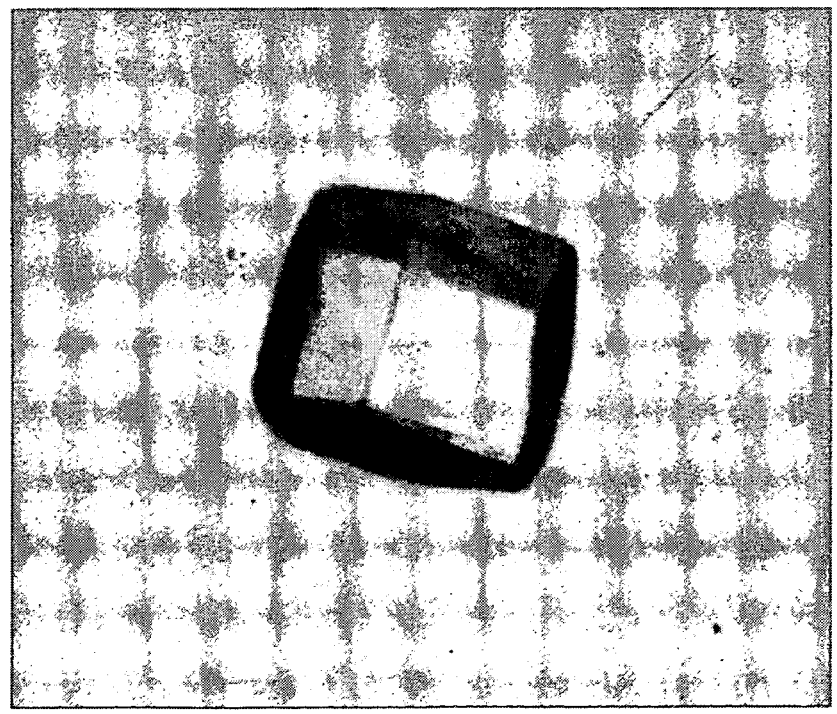
FIG. 10 is an optical micrograph of a lysozyme crystal produced in Example 3.

An about 0.2 mm cubic lysozyme crystal together with 70 μl of egg white lysozyme solution was set on a gold-deposited surface in the inner vessel of a dialysis cell. The chicken egg white lysozyme solution in the inner vessel and the buffer solution filled the dialysis outer liquid chamber were the same as those used in Example 2. In the same manner as that in Example 2, the mixing ratio of the precipitating agent solution and the buffer solution was changed to control the concentration of NaCl in the inner vessel. Based on the information on the solubility curve of lysozyme obtained in Example 1 (cf., FIG. 8), the crystal was grown while simultaneously measuring the concentration of the protein and the concentration of NaCl and maintaining the degree of supersaturation between 1.0 to 1.5. As a result, a relatively large, high-quality crystal of about 1 mm cubic was obtained. The optical micrograph of the obtained crystal is shown in FIG. 10.

INDUSTRIAL APPLICABILITY

According to the present invention, the solubility of protein crystals can be measured with an extremely small amount of protein used in a short time without the fear of denaturation of the protein and with accuracy.

Further, the present invention has excellent effects of producing high-quality protein crystals reliably and extremely efficiently by controlling the conditions of growing protein, crystals, in particular the degree of supersaturation to desired conditions by using a highly reliable solubility curve prepared by using accurate numerical values of solubility obtained.

The invention claimed is:

1. An apparatus of producing a protein crystal, comprising:
a dialysis cell for containing a protein crystal and a protein solution filled around the protein crystal, the dialysis cell comprising (i) a quartz thin plate for mounting the protein crystal, provided with a light reflecting thin film on a portion of a surface thereof, (ii) an inner vessel for containing the quartz thin plate therein, provided with a surface portion covered with a dialysis membrane and filled with the protein solution therein, and (iii) an outer vessel filled with the protein precipitating agent solution outside the dialysis membrane;
a protein solution inflow source selector for controlling a concentration of the protein in the protein solution around the protein crystal, the selector being capable of repeatedly switching between a protein solution and a diluent source for introduction into the dialysis cell;
a protein concentration measurement device for measuring a concentration of the protein solution around the protein crystal;
a two-beam interferometer for observing interference fringes around the protein crystal;
a precipitating agent concentration measurement device for measuring the concentration of the precipitating agent in the dialysis cell;
a precipitating agent inflow concentration control element for controlling a concentration of the precipitating agent in the protein solution around the protein crystal, the control element adjusting the concentration of the precipitating agent for introduction into the dialysis cell, in response to concentration measurements from the precipitating agent concentration measurement device.

2. The apparatus according to claim 1, wherein the protein concentration measurement device is a spectrophotometer.

3. The apparatus according to claim 2, wherein the spectrophotometer measures an intensity of transmitted light that transmits a portion of the quartz thin plate in the dialysis cell where light reflecting thin film is not provided.

4. The apparatus according to claim 2, wherein the outer vessel comprises the precipitating agent inflow element for sending the precipitating agent solution having a desired concentration to the outer vessel of the dialysis cell.

5. The apparatus according to claim 2, further comprising wherein the inner vessel comprises the protein solution inflow element for introducing the protein solution having a desired concentration into the inner vessel of the dialysis cell without disassembling the dialysis cell.

6. The apparatus according to claim 1, further comprising a photography device for photographing the interference fringes by the two-beam interferometer.

7. The apparatus according to claim 1, wherein the two-beam interferometer is a Michelson type two-beam interferometer.

8. An apparatus of producing a protein crystal, comprising:
an outer vessel having (i) a chamber and (ii) an inlet for introducing a precipitating agent into the chamber;
an inner vessel removably positioned within the chamber of the outer vessel, the inner vessel having (i) an interior for containing the protein crystal, surrounded by a protein solution, (ii) an inlet for introducing the protein solution into the interior;
a dialysis membrane, the interior of the inner vessel and the chamber of the outer vessel being separated by the dialysis membrane;

a quartz thin plate for mounting the protein crystal, the plate having a light reflecting thin film on a portion thereof and being removably positioned in the interior of the inner vessel;

an inner vessel inlet source selector for switching between a protein solution and a diluent for introduction into the inner vessel inlet, the selector providing control of protein solution concentration in the inner vessel;

a protein concentration measurement device for measuring a concentration of the protein solution in the inner vessel;

a two-beam interferometer for observing interference fringes around the protein crystal in the inner vessel;

a precipitating agent concentration measurement device for measuring the concentration of the precipitating agent of the outer vessel;

an outer vessel inlet concentration control element for adjusting a concentration of the precipitating agent for introduction into the outer vessel inlet, in response to concentration measurements from the precipitating agent concentration measurement device.

* * * * *